United States Patent [19]
Simpson

[11] Patent Number: 5,980,570
[45] Date of Patent: Nov. 9, 1999

[54] SYSTEM AND METHOD FOR IMPLANTING AN EXPANDABLE MEDICAL DEVICE INTO A BODY

[75] Inventor: Charles Lee Simpson, Austin, Tex.

[73] Assignee: Sulzer Carbomedics Inc., Austin, Tex.

[21] Appl. No.: 09/049,411

[22] Filed: Mar. 27, 1998

[51] Int. Cl.⁶ .................................................. A61F 2/24
[52] U.S. Cl. .................................................. 623/2; 623/3
[58] Field of Search ........................... 623/2, 3; 128/640, 128/772; 606/92, 93

[56] References Cited

U.S. PATENT DOCUMENTS

| | | | |
|---|---|---|---|
| 3,875,595 | 4/1975 | Froning | 128/92 |
| 5,037,442 | 8/1991 | Wintermantel et al. | 623/23 |
| 5,236,460 | 8/1993 | Barber | 623/17 |

*Primary Examiner*—David H. Willse
*Assistant Examiner*—Suzette J. Jackson
*Attorney, Agent, or Firm*—Philip S. Lyren; Kenneth S. Barrow; Timothy L. Scott

[57] ABSTRACT

A system and method are disclosed for implanting a medical device (12) into a body. The medical device (12) has an expanded state and a collapsed state and is inserted into the body while in the collapsed state. The medical device (12) is positioned proximate a desired implant site (14) in the body, and the medical device (12) is expanded to the expanded state by filling the medical device (12) with a hardenable fluid (18). The hardenable fluid (18) is then hardened such that the medical device (12) is set in the expanded state at the desired implant site (14).

16 Claims, 2 Drawing Sheets

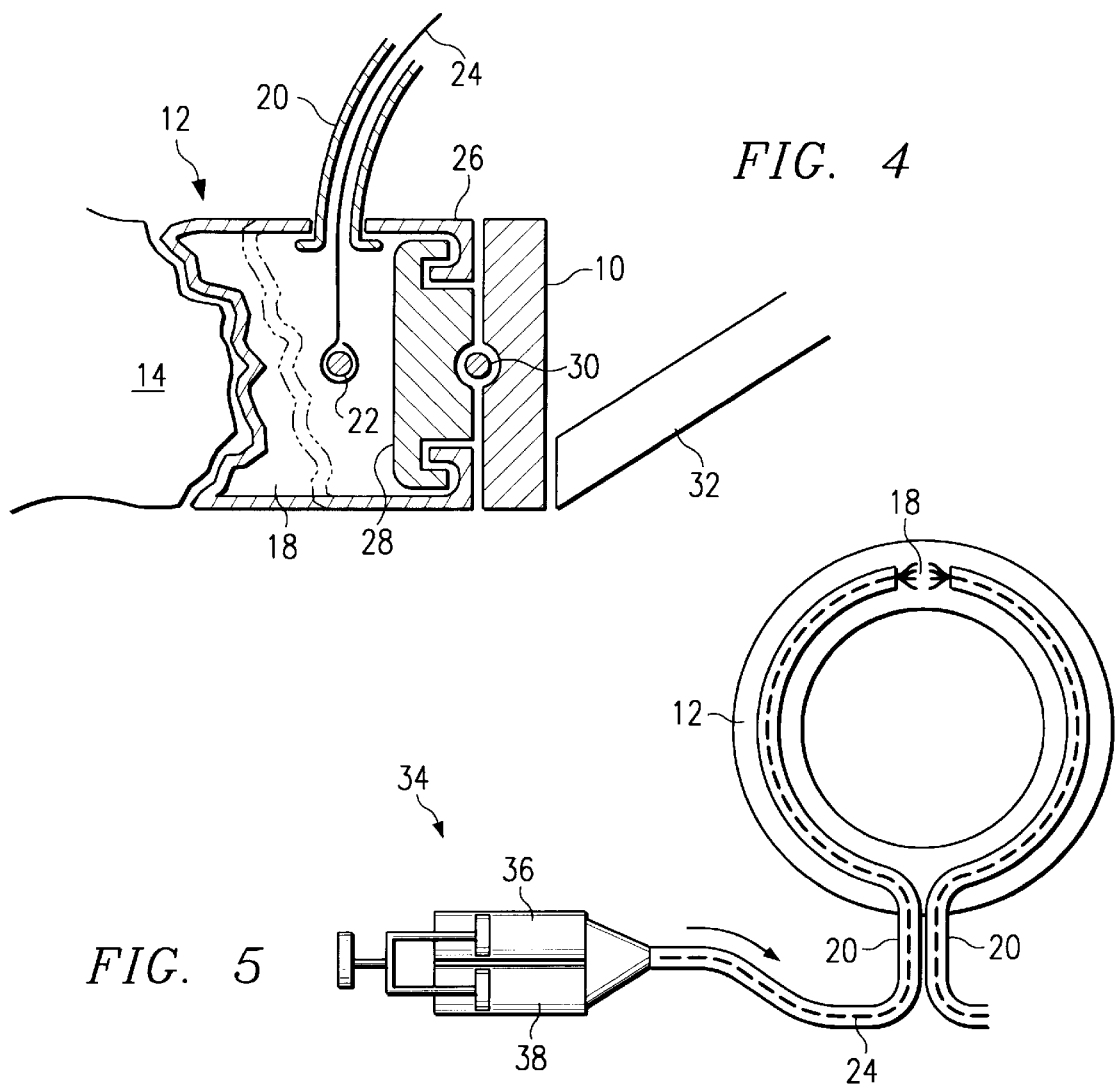
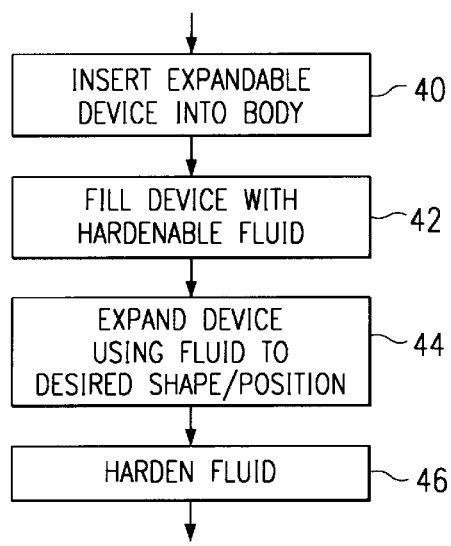

SYSTEM AND METHOD FOR IMPLANTING AN EXPANDABLE MEDICAL DEVICE INTO A BODY

TECHNICAL FIELD OF THE INVENTION

The present invention relates in general to the field of implantation of medical devices, and, more particularly, to a system and method for implanting an expandable medical device into a body.

BACKGROUND OF THE INVENTION

The implantation of medical devices is a procedure used for a variety of purposes including correcting or alleviating a wide variety of cardiac and orthopedic conditions. For example, artificial joints are used to replace old or damaged joints, stents are used to expand and support weak and narrow arteries, pacemakers are used to monitor and correct heart beat irregularities and artificial heart valves are used to replace improperly functioning heart valves.

One problem with the implantation procedures in general is that the surgery can be particularly invasive and present a difficult recovery. For example, in the case of heart valves, a typical surgery is an open heart procedure. The trauma caused by the surgeons efforts to reach the implant site can be very difficult and painful for recovery. Another problem is affixing the medical device once positioned at the implant site. For example, heart valves are often affixed using a sewing cuff and sutures. Consequently, the affixation process can be detailed and time-consuming adding to the length of the procedure. It is therefore desirable to provide improved implantation methods that can be accomplished through less invasive and time consuming procedures.

SUMMARY OF THE INVENTION

In accordance with the present invention, a system and method are disclosed for implanting an expandable medical device into a body that provides significant advantages over conventional implant devices and methods.

According to one aspect of the present invention, the method includes inserting a medical device having an expanded state and a collapsed state into the body while in the collapsed state. The medical device is positioned proximate a desired implant site in the body, and the medical device is expanded to the expanded state by filling the medical device with a hardenable fluid. The hardenable fluid is then hardened such that the medical device is set in the expanded state at the desired implant site.

According to another aspect of the present invention, the system includes a source for hardenable fluid that is coupled in fluid communication with the medical device. The medical device can be inserted into the body while in the collapsed state and positioned proximate a desired implant site in the body. The source can be used to fill the medical device with the hardenable fluid and thereby expand the medical device to the expanded state. Subsequently, the hardenable fluid can be hardened such that the medical device is set in the expanded state at the desired implant site.

A technical advantage of the present invention is the ability to implant a medical device percutaneously or through a relatively small endoscopic port because of the small size of the medical device while in the collapsed state. The expandability of the device allows a relatively large device to be implanted through a relatively small hole while in the collapsed state.

Another technical advantage of the present invention is that the medical device can be expanded to engage an implant site and form an interference fit. Thus, the medical device can be affixed without or with less sutures or other attachment means.

Other technical advantages of the present invention should be apparent from the drawings, description and claims.

BRIEF DESCRIPTION OF THE DRAWINGS

A more complete understanding of the present invention and advantages thereof may be acquired by referring to the following description taken in conjunction with the accompanying drawings, in which like reference numbers indicate like features, and wherein:

FIG. 4 is a cross section diagram of one embodiment of affixing a heart valve device according to the present invention;

FIG. 5 is a diagram of one embodiment of a source for hardenable fluid according to the present invention; and FIG. 6 is a flow chart of one embodiment of a method for implanting an expandable medical device according to the present invention.

DETAILED DESCRIPTION OF THE INVENTION

Figure 1:
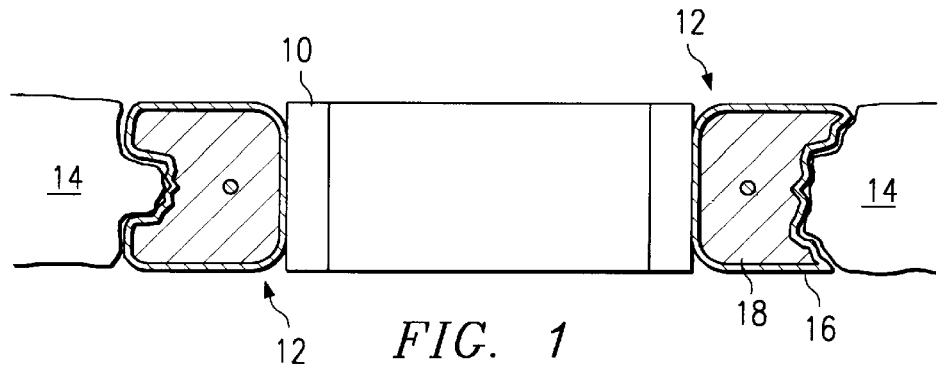
FIG. 1 is a cross section of one embodiment of a heart valve device implanted according to the present invention.

FIG. 1 is a cross section of one embodiment of a heart valve device implanted according to the present invention. As shown, an artificial heart valve device 10 and an annular ring 12 are positioned in a valve annulus 14. Valve annulus 14 is an implant site formed by the removal of the patient's existing heart valve. In FIG. 1, heart valve device 10 is held in place by annular ring 12 which engages valve annulus 14 in an interference fit. Annular ring 12 could further be held in place using sutures if necessary. In the illustrated embodiment, annular ring 12 comprises a polymer casing 16 filled with cured epoxy 18. Prior to implantation and hardening of epoxy 18, annular ring 12 was expandable due to the flexibility of polymer casing 16. Annular ring 12 had a collapsed state and an expanded state. Because annular ring 12 can be collapsed, annular ring 12 can be fed through a smaller opening than would be required by its expanded size. After positioning at valve annulus 14, annular ring 12 was expanded from its collapsed state by filling annular ring 12 with uncured epoxy 18. In its expanded state, annular ring 12 both engages valve annulus 14 and holds heart valve 10, as one. Once annular ring 12 was expanded, epoxy 18 was hardened to cured epoxy 18. Annular ring 12 was thus affixed at the implant site holding the new heart valve 10 in place. It should be understood that annular ring 12 could be formed from flexible or expandable materials other than a polymer and could be filled with hardenable fluids other than epoxy. Further, it should be understood that types of medical devices other than artificial heart valves could be implemented using an expandable medical device and hardenable fluid.

Figure 2:
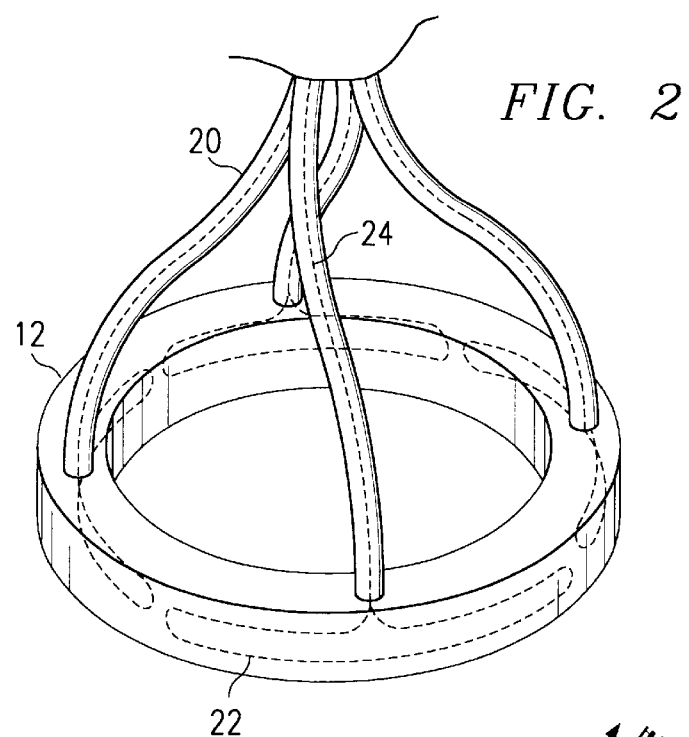
FIG. 2 is a perspective view of one embodiment of catheters used to fill an expandable medical device according to the present invention.

FIG. 2 is a perspective view of one embodiment of catheters used to fill an expandable medical device according to the present invention. As shown, a plurality of filler delivery catheters 20 can be coupled in fluid communication with annular ring 12. Catheters 20 are operable to fill annular ring 12 with a hardenable fluid obtained from a source to which catheters 20 are coupled. In the illustrated embodiment, annular ring 12 has a heating element 22 positioned within it, and a heating element 24 extends through each catheter 20.

In operation, catheters 20 are used to deliver the hardenable fluid, such as an epoxy, to annular ring 12 to expand annular ring 12 to its expanded state. Once the annular ring 12 is in the desired shape and position at the implant site, heating elements 22 and 24 can be used to heat the hardenable fluid to increase the rate of hardening. As the fluid hardens, heating elements 24 can be detached from heating element 22, and catheters 20 can be removed from annular ring 12 and from the patient's body. After removal of catheters 20, the fluid completes its hardening process, and annular ring 12 is set in the expanded state at the desired implant site. Heating element 22 is left in annular ring 12 after curing and can be used, for example, for radio imaging to ensure that the implanted medical device remains in the appropriate position.

Figure 3A:
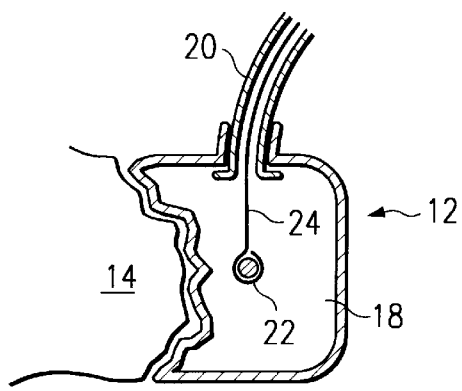
FIGS. 3A and 3B are cross section views of one embodiment of a catheter coupled to fill an expandable medical device according to the present invention.
Figure 3B:
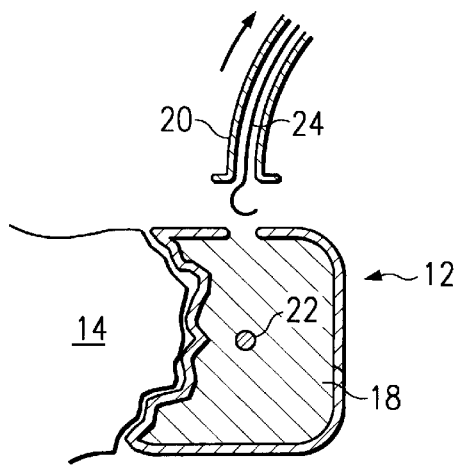

FIGS. 3A and 3B are cross section views of one embodiment of a catheter coupled to fill an expandable medical device according to the present invention. As shown in FIG. 3A, catheter 20 can extend through a port formed in annular ring 12. Also, heating element 24 can be connected to heating element 22. Annular ring 12 can then be filled with a hardenable fluid 18, such as an epoxy, to expand annular ring 12 to its desired shape. In the illustrated embodiment, annular ring 12 is expanded to provide an interference fit with valve annulus 14. Referring to FIG. 3B, hardenable fluid 18 has hardened to the point where catheter 20 needs to be removed. Heating element 24 is detached from heating element 22, and catheter 20 is removed from the port in annular ring 12. The edges of the port in annular ring 12 can then fold down to substantially cover the port. Because fluid 18 has hardened significantly, no significant amount of fluid 18 will escape from the port after the removal of catheter 20. In this embodiment, fluid 18 is partially cured by applying an electric current to heating elements 24 and 22. It should be understood that there are other possibilities for applying electric current to annular ring 12 and for increasing the cure rate of hardenable fluid 18.

FIG. 4 is a cross section diagram of one embodiment of affixing a heart valve device according to the present invention. As shown, a heart valve device 10 is implanted using expandable annular ring 12 which forms an interference fit with valve annulus 14. Catheter 20 is used to fill annular ring 12 with a hardenable fluid 18, and heating elements 22 and 24 are used to heat and speed curing of fluid 18. As shown, annular ring 12 has a shell 26 that has a pair of rims to engage a titanium stiffener ring 28. Stiffener ring 28 and device 10 have opposing ridges in which a locking wire 30 is positioned. Locking wire 30 thus engages stiffener ring 28 and device 10 and holds device 10 in place with respect to annular ring 12. This ensures that device 10 along with its leaflets 32 are appropriately positioned within valve annulus 14.

FIG. 5 is a diagram of one embodiment of a source for hardenable fluid according to the present invention. As shown, a source 34 for a hardenable fluid comprises an epoxy delivery device having a first chamber 36 and a second chamber 38. Chambers 36 and 38 are typical for epoxy delivery and hold the separate components of the epoxy. In the embodiment of FIG. 5, annular ring 12 is expanded by flow of epoxy from catheters 20 which extend through the interior of annular ring 12. Catheters 20 can be withdrawn as epoxy exits catheters 2 to provide for a complete filling of annular ring 12.

FIG. 6 is a flow chart of one embodiment of a method for implanting an expandable medical device according to the present invention. In step 40, the medical device is inserted into the body. The medical device has an expanded state and a collapsed state and is inserted while in the collapsed state. The medical device is also positioned proximate the desired implant site in the body. In step 42, the medical device is filled with a hardenable fluid. The medical device is expanded in step 44 to the desired shape and position by filling with the hardenable fluid. Then, in step 46, the hardenable fluid is hardened such that the medical device is set in the expanded state at the desired implant site. In one implementation, the hardenable fluid is a curable epoxy, and hardening is speeded by heating the hardenable fluid. Further, the filling and expanding can be accomplished by injecting the hardenable fluid into the medical device using a filler delivery catheter. In order to affix the medical device at the implant site, the expanding and hardening of the medical device can produce an interference fit between the medical device and the implant site. Alternatively, the medical device can be sutured at the implant site after hardening. As mentioned above, in one implementation, the medical device can be an annular ring, and the implant site can be a valve annulus formed after removal of a heart valve where the annular ring holds a heart valve device in place in the valve annulus. Alternatively, the medical device can be a whole heart valve device or other medical device.

The use of an expandable medical device according to the present invention provides significant advantages. The device can be used, for example, as an attachment mechanism for heart valve device, annuloplasty ring, vascular stent or septal defect repair device. In situ, the medical device is expanded with a fluid that can be hardened to a solid. During expansion, the medical device can conform to the shape of the annulus or other implant site to form an interference fit. After expansion, the fluid filler material is transformed to a solid, and the filler delivery catheter or other filler mechanism can be removed. The collapsed size of the medical device allows it to be used, for example, both during a conventional open heart procedure or during an endoscopic port procedure. Further, when compared with traditional suturing methods, the expandable device provides an easier procedure requiring less surgical time. Further, the device can be percutaneously delivered and operated remotely with the use of catheters to avoid the necessity, for example, of an open heart procedure.

With respect to artificial heart valves, the expandable annular ring can be used, for example, either pre-attached or attached in situ to a heart valve. The expandable annular ring can be filled with a fluid that can be sufficiently hardened within a few minutes to form an interference fit with the irregularly shaped valve annulus. As mentioned above, one method for curing the fluid is to use a urethane epoxy that can be cured with the application of heat. After filling, an electrical current could be applied. The heat produced cures the center core of the epoxy but does not transmit excessive heat to the exterior. Thus, the native annulus would not be subjected to potentially tissue damaging heat. The curing of the core is sufficient to provide enough stiffness to hold the device in place while the remainder of the epoxy cures due to a chemical reaction between the epoxy and catalyst. For example, ASTM F602 Standard Criteria for Implantable Thermoset Epoxy Plastics describes thermoset plastics based on diglycidyl ethers of bisphenol A (DGEBPA). These materials have a history of use and demonstrated biocompatibilty in implantable devices such as pacemakers and vascular access devices. These materials are available in a two component, solvent-free form that when subjected to elevated temperatures, will begin to harden within 10–15 minutes and completely cure within 30–40 minutes. An alternate embodiment is to use a UV light curable material that could be cured with light energy delivered via a light bundle as opposed to using a wire heating element.

Another consideration is that the expandable medical device needs to be biocompatible and biostable. Further, the device must be capable of inducing controlled tissued growth at selected sites such as the area of contact with the annulus wall. Also, the device needs to be capable of withstanding the pressure required to inject the hardenable fluid without rupture or significant leakage. Polymeric materials such as silicone or polyurethane can be suitable. Further, the hardenable fluid needs to be capable of being delivered in a fluid form and be readily transformed into a solid. In solid form, the material needs to be biocompatible and biostable and should have sufficient strength to maintain the mechanical capture with the native annulus or other implant site. Additionally, in the example of a heart valve, the material adjacent to the inflow and outflow sides of the valve should either induce an endothelial covering or pseudo-intimal lining to form without excessive pannus tissue formation and growth, or alternatively, the material should remain tissue free and be non-thrombogenic.

Although the present invention has been described in detail, it should be understood that various changes, substitutions, or alterations can be made thereto without departing from the spirit and scope of the invention as defined by appended claims.

What is claimed is:

1. A method for implanting a heart valve into a body, comprising:
   inserting a heart valve into the body, the heart valve having an expanded state and a collapsed state, where the heart valve is inserted while in the collapsed state;
   positioning the heart valve proximate a desired implant site in the body;
   expanding the heart valve to the expanded state by filling the heart valve with a hardenable fluid; and
   hardening the hardenable fluid such that the heart valve is set in the expanded state at the desired implant site.

2. The method of claim 1, wherein the hardenable fluid is a curable epoxy.

3. The method of claim 1, wherein hardening comprises heating the hardenable fluid.

4. The method of claim 3, wherein the heating is accomplished using a heating element.

5. The method of claim 1, wherein expanding is accomplished by injecting the hardenable fluid into the heart valve using a filler delivery catheter.

6. The method of claim 1, wherein the expanding and hardening of the heart valve produces an interference fit between the medical device and the implant site.

7. The method of claim 1, further comprising suturing the heart valve at the implant site after hardening.

8. The method of claim 1, wherein:
   the heart valve has an annular ring and the implant site is a valve annulus formed after removal of a natural heart valve in the body; and
   the annular ring holds the heart valve device in place in the valve annulus.

9. A system for implanting a heart valve into a body, comprising:
   a heart valve having an expanded state and a collapsed state; and
   a source for hardenable fluid, the source coupled in fluid communication with the heart valve;
   the heart valve operable to be inserted into the body while in the collapsed state and positioned proximate a desired implant site in the body;
   the source operable to fill the heart valve with the hardenable fluid and thereby expand the heart valve to the expanded state; and
   the hardenable fluid operable to harden such that the heart valve is set in the expanded state at the desired implant site.

10. The system of claim 9, wherein the hardenable fluid is a curable epoxy.

11. The system of claim 9, wherein the hardenable fluid is hardened by heating the hardenable fluid.

12. The system of claim 11, further comprising a heating element used to heat the hardenable fluid.

13. The system of claim 9, wherein the source is coupled to the heart valve using a filler delivery catheter.

14. The system of claim 9, wherein expanding and hardening of the heart valve produces an interference fit between the medical device and the implant site.

15. The system of claim 9, wherein the heart valve is operable to be sutured at the implant site after hardening.

16. The method of claim 1, wherein:
   the heart valve has an annular ring and the implant site is a valve annulus formed after removal of a natural heart valve in the body; and
   the annular ring holds the heart valve device in place in the valve annulus.

* * * * *